(12) United States Patent
Breu et al.

(10) Patent No.: US 7,544,691 B2
(45) Date of Patent: Jun. 9, 2009

(54) GUANIDINE DERIVATIVES

(75) Inventors: Volker Breu, Schliengen (DE); Anja Fecher, Weil am Rhein (DE); Heinz Fretz, Riehen (CH); Thomas Giller, Wintersingen (CH); Kurt Hilpert, Hofstetten (CH); Olivier Valdenaire, Allschwil (FR)

(73) Assignee: Actelion Pharmaceuticals, Ltd., Allschwil (CH)

( * ) Notice: Subject to any disclaimer, the term of this patent is extended or adjusted under 35 U.S.C. 154(b) by 153 days.

(21) Appl. No.: 10/570,517

(22) PCT Filed: Sep. 3, 2004

(86) PCT No.: PCT/CH2004/000556

§ 371 (c)(1),
(2), (4) Date: Nov. 2, 2006

(87) PCT Pub. No.: WO2005/023781

PCT Pub. Date: Mar. 17, 2005

(65) Prior Publication Data

US 2007/0123510 A1 May 31, 2007

(51) Int. Cl.
*A61K 31/517* (2006.01)
(52) U.S. Cl. .................................. 514/266.4; 544/292
(58) Field of Classification Search .................. 544/292
See application file for complete search history.

(56) References Cited

U.S. PATENT DOCUMENTS

| 3,505,327 A | | 4/1970 | Miller et al. |
| 4,880,932 A | * | 11/1989 | Moriya et al. ............... 544/320 |
| 2003/0139431 A1 | | 7/2003 | Kawakami et al. |

FOREIGN PATENT DOCUMENTS

| DE | 22 06 385 C2 | 2/1972 |
| DE | 2 206 385 | 8/1973 |
| WO | WO-03/026667 A1 | 4/2003 |
| WO | WO 03/026667 | 7/2003 |

OTHER PUBLICATIONS

Baldwin, John E. et al; "Quantitative Analyses of the Seven Isomeric 3,4- and 3,6-Dimethylcyclohexenes by Gas Chromatography"; J. Org. Chem. vol. 65, No. 21, 2000, pp. 7145-7150.
Hajos, Gyorgy et al.; "Synthesis and Chiroptical Properties of 5α-Cholest-2-Eno[2,3-b]Pyrazine Derivatives"; Heterocycles, vol. 28, No. 2, 1989, pp. 783-789.
Kaiho, Tatsuo et al.; "Cardiotonic Agents. 1-Methyul-7-(4-pyridyl)-5,6,7,8-tetrahydro-3(2H)-isoquinolinones and Related Compounds. Synthesis and Activity1"; Journal of Medicinal Chemistry, 1989, vol. 32, No. 2, pp. 351-357.
Meth-Cohn, Otto et al; "A Versatile New Synthesis of Quinolines and Related Fused Pyridines. Part 12.1 A General Synthesis of 2-Chloropyridines and 2-Pyridones"; J. Chem. Soc. Perkin Trans. I (1984), pp. 1173-1182.
Panula, Pertti et al; "Neuropeptide FF, A Mammalian Neuropeptide With Multiple Functions"; Progress in Neurobiology vol. 48 (1996), pp. 461-487.
Roumy, Michel et al.; "Neuropeptide FF, pain and analgesia"; European Journal of Pharmacology 345 (1998), pp. 1-11.
Secor, Henry et al; "Synthesis and Screening of Some Trifluoromethyl Pyrazoles"; Journal of Medicinal Chemistry, 1971, vol. 14, No. 10, pp. 997-998.
Sontjens, Serge et al; "A Multiple Hydrogen-Bond Scaffold Based on Dipyrimidin-2-ylamine"; Organic Letters 2001, vol. 3, No. 24, pp. 3887-3889.
Thesing and Muller; Uber Eine Neue Methode Zur Darstellung Von α-Pyridonen Und Die Synthese Des Nicotellins; Chem. Ber. (1957), 90, pp. 711-723.
Vijn, Robert J. et al; "Synthesis of 6-Substituted 2-(N-Acetylamino)pyridines and 2-Aminopyridines by Cyclization of 5-Oximinoalkanenitriles"; J. Org. Chem., vol. 58, No. 4, 1993, pp. 887-891.
Yokoo, Akira et al; "Studies on Seven-membered Heterocyclic Compounds Containing Nitrogen. I. Synthesis of 1-Azacycloheptan-4 one Hydrochloride"; Bull. Chem. Soc. Japan (Jul. 1956), vol. 29, No. 5, pp. 631-632.
Lefrere et al.; "Neuropeptide AF and FF Modulation of Adipocyte Metabolism"; The Journal of Biological Chemistry, vol. 277, No. 42, Issue of Oct. 18, 2002, pp. 39169-39178.

* cited by examiner

*Primary Examiner*—James O Wilson
*Assistant Examiner*—Brian McDowell
(74) *Attorney, Agent, or Firm*—Hunton & Williams LLP

(57) ABSTRACT

The invention relates to the guanine derivatives of general formula (I), and to hydrates or solvents thereof, for use as neuropeptide FF receptor antagonists in the treatment of pains and hyperalgesia, of withdrawal symptoms of addiction to alcohol, psychotropic drugs or nicotine and in the prevention of or recovery from these addictions, for the regulation of insulin release, food intake, memory functions, blood pressure, electrolyte and energy metabolism, and in the treatment of urinary incontinence (I)

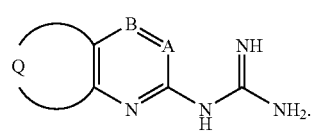

9 Claims, No Drawings

GUANIDINE DERIVATIVES

The present invention relates to guanidine derivatives of general formula

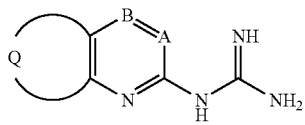

in which
A represents CH or N;
B represents N or a C atom substituted with $R_1$;
Q represents a chain of 3-6 optionally substituted C atoms, one or more of which can be replaced by —N(R')—, —O— or —S(O)$_m$—, in the case of many such atoms or groups these being able to be identical or different;
$R_1$, R' represents hydrogen or a substituent; and
m represents 0, 1 or 2;

pharmaceutically acceptable acid addition salts of basic compounds of formula I, pharmaceutically acceptable salts of acid group-containing compounds of formula I with bases, pharmaceutically acceptable esters of hydroxy or carboxy group-containing compounds of formula I as well as hydrates or solvates thereof.

These compounds are novel, and they are characterized by valuable pharmacodynamic properties. They act as neuropeptide FF receptor antagonists and are suitable for the treatment of pain, for the control of hypersensitivity to pain (hyperalgesia), chronic, acute, long-lasting or temporary pain, these pains being able to be of operative, traumatic, or pathological origin, with the advantage of preventing or curing opioid tolerance and/or opioid dependence. The substances according to the invention are also suitable for the treatment of withdrawal symptoms in the case of alcohol, psychotropics and nicotine dependences and for the prevention or elimination of these dependences. The compounds can additionally be used for the regulation of insulin secretion, food intake, memory functions, blood pressure, and of the electrolyte and energy balance and for the treatment of urinary incontinence.

Guanidine derivatives of Formula I, which contain one or more asymmetric centres, can be present as optically pure enantiomers, as mixtures of enantiomers, such as for example racemates, or optionally as optically pure diastereomers, as mixtures of diastereomers, as diastereomeric racemates or as mixtures of diastereomeric racemates.

The FF (NPFF), AF (NPAF), SF (NPSF) and VF (NPVF) neuropeptides are related neurotransmitters with pain-modulating properties. Together with the recently discovered G-protein coupled receptors, NPFF1 and NPFF2, they form a large part of an endogenous system, which regulates sensitivity to pain in various types of mammals such as humans, rats, mice, cattle etc. Said neuropeptides appear to play an important role both in opioid-dependent analgesia and in the development of tolerance to opioids (review article: Roumy and Zajac, Europ. J. Pharm. 1998, 345, 1-11; Panula et al., Prog. Neurobiol. 1996, 48, 461-87). According to other reports NPFF also appears to play a role in physiological processes such as insulin secretion, regulation of food intake, memory functions, blood pressure and electrolyte balance (Panula et. al., Prog. Neurobiol. 1996, 48, 461-487).

The incidence of functional NPFF1 and NPFF2 receptors in adipocytes and the effect of NPFF and NPAF on key sites of signal transmission in the adipose metabolism suggest that the two peptides, alongside their original pain-modulating effects, could also have an influence on the storage and use of body energy (Lefrère et al., J. Biol. Chem. 2002, 277 (42), 39169).

The current options for treatment of chronic pain are based on NSAIDs (non-steroidal anti-inflammatory drugs), canabinoids and opioids. Thus, for example, morphine derivatives bind to the μ-opioid receptor and thereby have an analgesic effect. Opioid binding to the μ-opioid receptor involves the release of neuropeptide FF. Based on animal experiments it is presumed that the released NPFF reduces the analgesic effect of the administered opioids and leads to tolerance to opioids. In order to obtain a constant analgesic effect with longer treatments, increasingly higher opioid doses must be administered as a result of this tolerance, which can finally lead to serious side effects. As already mentioned at the outset, to date two neuropeptide FF receptors are known, the NPFF1 receptor being located mainly in the central nervous system and the NPFF2 receptor in the spinal cord in particular. Activation of the NPFF2 receptors shows an opioid-like analgesic effect. Blocking of the NPPF1 receptors by an antagonist prevents the development of tolerance to opioids and also increases their effect.

Kawakami J. K. et al. (PCT Application WO03/026667, published 3 Apr. 2003) describe quinazoline guanidine and quinoline guanidine-derivatives as NPFF-receptor ligands.

As mentioned at the outset the substances according to the invention are novel and are characterized by valuable pharmacological properties. Because of their property of blocking the interaction of neuropeptide FF with the neuropeptide FF1 receptor subtype, the compounds of Formula I according to the invention and their pharmaceutically acceptable salts are suitable for a use as a medicinal product, in particular for the treatment of pain and hyperalgesia, with the substances according to the invention supplementing the current treatment methods for chronic pain, and with the advantage of preventing or curing undesirable opioid tolerance and/or dependence. The substances according to the invention are also suitable for the treatment of withdrawal symptoms in the case of alcohol, psychotropics and nicotine dependences and for the prevention or elimination of these dependences. They can additionally be used for the regulation of insulin secretion, food intake, memory functions, blood pressure, and of the electrolyte and energy balance and for the treatment of urinary incontinence.

A subject of the present invention is the novel substances as such and as therapeutic active ingredients; methods and intermediate products for their preparation; medicinal products containing one of the above substances; the preparation of such medicinal products; and the use of the above substances for the prevention and treatment of hypersensitivity to pain (hyperalgesia), chronic, acute, long-lasting or temporary pain, which can be of operative, traumatic, or pathological origin, of withdrawal symptoms in the case of alcohol, psychotropics and nicotine dependences and for the prevention or elimination of these dependences, for the regulation of insulin secretion, food intake, memory functions, blood pressure, and of the electrolyte and energy balance and for the treatment of urinary incontinence or for the preparation of corresponding medicinal products.

If B in Formula I is a C atom substituted with $R_1$, then the substituent $R_1$ can be hydrogen or a lower alkyl, haloalkyl, alkylamino, cycloalkylamino, alkoxy, haloalkoxy or alkylthio group. Preferred possible meanings for $R_1$ are methyl, ethyl, trifluoromethyl, methylamino, ethylamino, isopropylamino, cyclopropylamino, methoxy, ethoxy, trifluoromethoxy, methylsulphanyl and ethylsulphanyl, particularly preferred are methyl and trifluoromethyl.

If one or more of the C atoms in the chain Q in formula I is/are substituted, then
- one of the C atoms can carry one or two (i.e. geminal) identical or different substituents; or
- several of the C atoms can each carry one or two (i.e. geminal) identical or different substituents.

In Formula I, Q together with a pyrimidine ring can form a quinazoline, cyclopentapyrimidine, cycloheptapyrimidine, pyridopyrimidine, pyranopyrimidine, thiopyranopyrimidine, pyrimidoazepine or cyclooctapyrimidine skeleton, which contains only the three double bonds of the pyrimidine component, such as for example a 6,7-dihydro-5H-cyclopentapyrimidine, 5,6,7,8-tetrahydro-quinazoline, 6,7,8,9-tetrahydro-5H-cycloheptapyrimidine, 5,6,7,8,9,10-hexahydro-cyclooctapyrimidine, 6,7-dihydro-5H-pyrrolopyrimidine or 5,6,7,8-tetrahydro-pyridopyrimidine skeleton.

In Formula I, Q together with a pyridine ring can also form a pyrindine, quinoline, cycloheptapyridine, cyclooctapyridine, pyrrolopyridine, naphthyridine, pyridoazepine, furopyridine, pyranopyridine, thienopyridine or thiopyranopyridine skeleton, which contains only the three double bonds of the pyridine component, such as for example a 6,7-dihydro-5H-[1]pyrindine, 5,6,7,8-tetrahydro-quinoline, 6,7,8,9-tetrahydro-5H-cyclohepta[b]pyridine, 5,6,7,8,9,10-hexahydro-cycloocta[b]pyridine, dihydro-pyrrolopyridine, dihydrofuropyridine, dihydrothienopyridine or 1,2,3,4-tetrahydro-naphthyridine skeleton.

In Formula I, Q together with a pyrazine ring can additionally form a cyclopentapyrazine, pyrrolopyrazine, furopyrazine, thienopyrazine, quinoxaline, pyridopyrazine, pyranopyrazine, thiadiazanaphthalene, cycloheptapyrazine, triazabenzocycloheptene, oxadiazabenzocycloheptene, or thiadiazabenzocycloheptene skeleton, which contains only the three double bonds of the pyrazine component, such as for example a 6,7-dihydro-5H-cyclopentapyrazine, 5,6,7,8-tetrahydro-quinoxaline, 6,7,8,9-tetrahydro-5H-cycloheptapyrazine, 5,6,7,8,9,10-hexahydro-cyclooctapyrazine, 6,7-dihydro-5H-pyrrolopyrazine or 5,6,7,8-tetrahydro-pyridopyrazine skeleton.

In Formula I, Q together with a triazine ring can additionally form a dihydrocyclopentatriazine, tetrahydro-benzotriazine, tetrahydrocycloheptatriazine, dihydro-pyrrolotriazine or tetrahydro-pyridotriazine skeleton, which contains only the three double bonds of the triazine component, such as for example a 6,7-dihydro-5H-cyclopenta[1,2,4]triazine, 5,6,7,8-tetrahydro-benzo[1,2,4]triazine, 6,7,8,9-tetrahydro-5H-cyclohepta[1,2,4]triazine, 5,6,7,8,9,10-hexahydro-1,2,4-triaza-benzocyclooctene, 6,7-dihydro-5H-pyrrolo[3,4-e][1,2,4]triazine, 5,6,7,8-tetrahydro-pyrido[4,3-e][1,2,4]triazine or 5,6,7,8-tetrahydro-pyrido[3,4-e][1,2,4]triazine skeleton.

A subgroup of the compounds according to the invention can be represented by the general formula

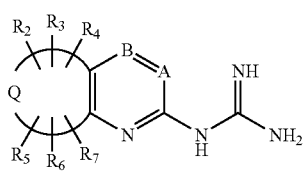

(II)

in which $R_2$-$R_7$ mean hydrogen, alkyl, alkanoyl, alkenyl, alkoxy, alkoxyalkyl, alkoxyalkanoyl, alkoxyalkylcarbamoyl, alkoxyalkylthiocarbamoyl, alkoxycarbonyl, alkoxycarbonylalkyl, alkoxycarbonylalkanoyl, alkylamido, alkylaminocarbonyl, alkylarylamino, alkylcarbamoyl, alkylthiocarbamoyl, alkylcarbonyl, alkylcarbonyloxy, alkylenedioxy, alkylsulphinyl, alkylsulphinylalkyl, alkylsulphonyl, alkylsulphonylalkyl, alkylthio, alkylsulphonamido, alkylthioalkyl, alkynyl, amino, aminoalkyl, aminoalkanoyl, aminoacyl, alkylamino, alkylaminoalkyl, alkylaminoalkanoyl, aminocarbonyl, aminocarbonylalkyl, aminocarbonylalkanoyl, alkylaminocarbonylamino, alkoxycarbonylamino, aryl, arylalkenyl, arylalkyloxy, arylalkyl, arylalkylamido, arylalkanoyl, arylamido, arylamino, arylaminocarbonyl, arylcarbamoyl, arylthiocarbamoyl, aryloxy, aryloxyalkyl, aryloxyalkanoyl, aryloxyalkylamino, aryloxyalkylcarbamoyl, aryloxyalkylthiocarbamoyl, aryloxycarbonyl, aryloxycarbonylalkyl, aryloxycarbonylalkanoyl, aryloxycarbonylalkylamino, aryloxycarbonylalkylcarbamoyl, aryloxycarbonylalkylthiocarbamoyl, arylsulphinyl, arylsulphinylalkyl, arylsulphonyl, arylsulphonylalkyl, arylsulphonylalkanoyl, arylsulphonamido, arylthio, arylthioalkyl, arylthioalkanoyl, carboxy, carboxyl, carboxyalkyl, carboxyalkylamido, cyano, cyanoalkyl, cyanoalkylamido, cyanoalkanoyl, cycloalkyl, cycloalkylamido, cycloalkanoyl, cycloalkylamino, cycloalkylaminocarbonyl, cycloalkyloxyalkyl, cycloalkyloxycarbonyl, cycloalkyloxycarbonylalkyl, cycloalkyloxycarbonylalkylamido, cycloalkyloxycarbonylalkanoyl, dialkylaminocarbonyl, dialkylaminoalkyl, dialkylaminoalkylamido, dialkylaminoalkanoyl, diarylamino, formyl, formylalkyl, halogen, haloalkoxy, haloalkyl, haloalkylamido, haloalkanoyl, haloalkylamino, heteroarylamino, heteroarylamido, heterocyclylalkylamido, heteroarylaminocarbonyl, heteroaryloxycarbonylalkyl, heteroaryloxycarbonylalkylamido, heteroaryloxycarbonylalkanoyl, heterocyclyl, heterocyclylamino, heterocyclylamido, heterocyclylalkyl, heterocyclylalkanoyl, heterocyclylalkylamino, heterocyclylalkylamido, heteroarylalkyl, heteroarylalkanoyl, heteroarylalkylamino, heteroarylalkylamido, heteroyclylalkylaminocarbonyl, heterocyclylalkoxycarbonylalkyl, heterocyclylalkoxycarbonylalkanoyl, heterocyclylalkoxycarbonylalkylamino, heterocyclylalkoxycarbonylalkylamido, hydroxy, hydroxyalkyl, hydroxyalkanoyl, mercapto or nitro.

Preferred possible meanings for $R_2$ are methyl, ethyl, n-propyl, isopropyl, n-butyl, isobutyl, tert-butyl, 1,1-dimethylpropyl, or phenyl. If $R_3$-$R_7$ are different from hydrogen, then they preferably mean methyl or another low alkyl radical.

Another subgroup of the compounds according to the invention can be represented by the general formula

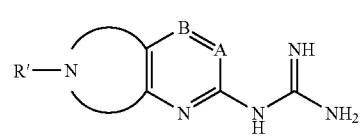

(III)

in which R' means alkyl, alkanoyl, alkenyl, alkinyl, alkoxycarbonylalkyl, alkoxycarbonylaminoalkanoyl, alkylcarbamoyl, alkoxycarbonylalkylcarbamoyl, alkoxycarbonylalkylthiocarbamoyl, alkylthiocarbamoyl, mono-or disubstituted aminoalkanoyl, aryl, arylalkyl, arylalkoxycarbonyl, arylalkanoyl, arylcarbamoyl, alkoxyalkanoyl, alkylsulphonyl, arylthiocarbamoyl, aryloxycarbonylalkyl, aryloxycarbonylalkanoyl, aryloxycarbonylalkylcarbamoyl, aryloxycarbonylalkylthiocarbamoyl, arylsulphonyl, cycloalkyl, cycloalkanoyl, cycloalkylcarbamoyl, cycloalkylthiocarbamoyl, cycloalkyl-carbonyl, cycloalkyloxycarbonylalkyl, cycloalkyloxycarbonylalkanoyl, cycloalkyloxycarbonylalkylcarbamoyl, cycloalkyloxycarbonylalkylthiocarbamoyl, heteroarylalkyl, heterocyclylalkyl, heterocyclylalkoxycarbonylalkyl, heterocyclylalkoxycarbonylalkanoyl, heterocyclylalkoxycarbonylalkylcarbamoyl, heterocyclylalkoxycarbonylalkylthiocarbamoyl, heteroaryloxycarbonylalkyl, heteroaryloxycarbonylalkylcarbamoyl or heteroaryloxycarbonylalkylthiocarbamoyl.

R' preferably means methyl, ethyl, propyl, hexyl, 2,2-dimethylpropionyl, cyclopropylmethyl, 2-cyclohexylethyl, propinyl, ethyloxycarbonylethyl, benzyl, n-butyloxycarbonyl, tert-butyloxycarbonyl, benzyloxycarbonyl, 3-methylbutyryl, pentanoyl, phenylacetyl, 2-propylpentanoyl, cyclopropanecarbonyl, isobutyryl, but-3-enoyl, 2-methoxyacetyl, propane-2-sulphonyl, butane-1-sulphonyl, methanesulphonyl, tert-butyloxycarbonylaminopropionyl or 4-dimethylaminobutyryl.

Quite particularly preferred compounds of Formula I are
rac-N-(4-methyl-6-propyl-5,6,7,8-tetrahydro-quinazolin-2-yl)-guanidine;
rac-N-(6-isopropyl-4-methyl-5,6,7,8-tetrahydro-quinazolin-2-yl)-guanidine;
rac-N-(4-methyl-5,6,7,8-tetrahydro-quinazolin-2-yl)-guanidine;
rac-N-(4,5-dimethyl-5,6,7,8-tetrahydro-quinazolin-2-yl)-guanidine and
rac-N-(6-tert-butyl-4-methyl-5,6,7,8-tetrahydro-quinazolin-2-yl)-guanidine.

Other particularly preferred compounds of Formula I are
rac-N-(4-methyl-8-phenyl-5,6,7,8-tetrahydro-quinazolin-2-yl)-guanidine;
rac-N-(4-methyl-6-phenyl-5,6,7,8-tetrahydro-quinazolin-2-yl)-guanidine;
rac-N-[6-(1,1-dimethyl-propyl)-4-methyl-5,6,7,8-tetrahydro-quinazolin-2-yl]-guanidine;
rac-N-(8-tert-butyl-4-methyl-5,6,7,8-tetrahydro-quinazolin-2-yl)-guanidine;
rac-N-(4,6-dimethyl-5,6,7,8-tetrahydro-quinazolin-2-yl)-guanidine;
rac-N-(4-methyl-6,7,8,9-tetrahydro-5H-cycloheptapyrimidin-2-yl)-guanidine;
rac-N-(4-methyl-5,6,7,8,9,10-hexahydro-cyclooctapyrimidin-2-yl)-guanidine and
rac-N-(8-sec-butyl-4-methyl-5,6,7,8-tetrahydro-quinazolin-2-yl)-guanidine.

Compounds of Formula I which are also preferred are
rac-N-(4,8-dimethyl-5,6,7,8-tetrahydro-quinazolin-2-yl)-guanidine;
rac-N-(8-allyl-4-methyl-5,6,7,8-tetrahydro-quinazolin-2-yl)-guanidine;
rac-N-(4-methyl-6,7-dihydro-5H-cyclopentapyrimidin-2-yl)-guanidine;
rac-N-(8-cyclohex-1-enyl-4-methyl-5,6,7,8-tetrahydro-quinazolin-2-yl)-guanidine;
rac-N-(6-isopropyl-5,6,7,8-tetrahydro-quinazolin-2-yl)-guanidine;
rac-N-(6-tert-butyl-5,6,7,8-tetrahydro-quinazolin-2-yl)-guanidine;
rac-N-(6-propyl-5,6,7,8-tetrahydro-quinazolin-2-yl)-guanidine;
rac-N-(6-phenyl-5,6,7,8-tetrahydro-quinazolin-2-yl)-guanidine; and
rac-N-(6-tert-butyl-4-trifluoromethyl-5,6,7,8-tetrahydro-quinazolin-2-yl)-guanidine.

Other representative compounds of Formula I are also
rac-N-[8-(2-cyano-ethyl)-4-methyl-5,6,7,8-tetrahydro-quinazolin-2-yl]-guanidine;
rac-2-guanidino-4-methyl-7,8-dihydro-5H-pyrido[4,3-d]pyrimidine-6-carboxylic acid tert-butyl ester;
rac-N-(6-phenyl-4-trifluoromethyl-5,6,7,8-tetrahydro-quinazolin-2-yl)-guanidine;
rac-N-(6-isopropyl-4-trifluoromethyl-5,6,7,8-tetrahydro-quinazolin-2-yl)-guanidine;
rac-N-(5,6,7,8-tetrahydro-quinolin-2-yl)-guanidine;
rac-N-(6-phenyl-5,6,7,8-tetrahydro-quinoline-2-yl)-guanidine;
rac-N-(5,6,7,8-tetrahydro-quinoxalin-2-yl)-guanidine;
rac-N-(6-phenyl-5,6,7,8-tetrahydro-quinoxalin-2-yl)-guanidine;
rac-N-(7-phenyl-5,6,7,8-tetrahydro-quinoxalin-2-yl)-guanidine;
rac-6,7,8-tetrahydro-benzo[1,2,4]triazin-3-yl)-guanidine;
rac-N-(7-phenyl-5,6,7,8-tetrahydro-benzo[1,2,4]triazin-3-yl)-guanidine and
N-(6-phenyl-5,6,7,8-tetrahydro-benzo[1,2,4]triazin-3-yl)-guanidine.

The term "alkyl", alone or in combination, describes a linear, branched or cyclic hydrocarbon radical with 1-8 C atoms. Representative, but not limitative, examples of alkyl are methyl, ethyl, n-propyl, i-propyl, n-butyl, t-butyl, i-butyl (or 2-methylpropyl), cyclopropylmethyl, n-pentyl, i-pentyl, i-amyl, n-amyl, n-hexyl, n-heptyl, n-octyl and the like. The alkyl radical can carry one or more substituents, which are chosen independently of each other from alkenyl, alkoxy, alkoxycarbonyl, alkylcarbonyl, alkylcarbonyloxy, alkylenedioxy, alkylsulphinyl, alkylsulphonyl, alkylthio, alkynyl, amino, aminocarbonyl, aryl, arylalkenyl, arylalkyloxy, aryloxy, aryloxycarbonyl, arylsulphinyl, arylsulphonyl, arylthio, carboxy, cyano, formyl, halogen, haloalkoxy, heterocyclyl, hydroxy, mercapto, nitro, and the like, which are linked via any carbon atom of the alkyl group.

The term "lower alkyl", alone or in combination, describes alkyl groups with 1-4 carbon atoms. Representative, but not limitative, examples of lower alkyl are methyl, ethyl, n-propyl, i-propyl, n-butyl, t-butyl and the like.

The term "alkenyl", alone or in combination, describes a linear or branched hydrocarbon radical with 2-8 C atoms, in which at least one carbon-carbon double bond ($R_aR_bC=CR_cR_d$) is present. $R_a$-$R_d$ describe substituents which are chosen independently of each other from hydrogen, alkyl, alkoxy, alkoxyalkyl, and the like. Representative, but not limitative, examples of alkenyl are ethenyl, 2-propenyl, 2-methyl-2-propenyl, 3-butenyl, 4-pentenyl, 5-hexenyl and the like.

The term "alkylenedioxy", alone or in combination, describes an —O($CH_2$)$_n$O group, in which n means 1 or 2, the o atoms being bound to two neighbouring C atoms of the main molecule skeleton. Representative, but not limitative examples of alkylenedioxy are methylenedioxy, ethylenedioxy and the like.

The term "alkynyl", alone or in combination, describes a linear or branched hydrocarbon radical with 2-8 C atoms, in which at least one carbon-carbon triple bond ($R_a$—C≡C—$R_b$) is present. $R_a$ and $R_b$ describe substituents which are chosen independently of each other from hydrogen, alkyl, alkoxy, alkoxyalkyl, and the like. Representative, but not limitative examples of alkynyl are acetylenyl, 1-propynyl, 2-propynyl, 1-butynyl, 3-butynyl, 2-pentynyl, and the like.

The term "alkoxy", alone or in combination, describes an alkyl group, which is linked via an oxygen bridge to the main skeleton. Representative, but not limitative examples of alkoxy are methoxy, ethoxy, propoxy, 2-propoxy, butoxy, t-butoxy, pentyloxy and hexyloxy.

The term "alkoxyalkyl", alone or in combination, describes an alkoxy group, which is linked via an alkyl radical. Representative, but not limitative examples of alkoxyalkyl are t-butoxymethyl, 2-ethoxyethyl, 2-methoxyethyl and methoxymethyl.

The term "alkoxycarbonyl", alone or in combination, describes an alkoxygroup, which is linked via a carbonyl group. Representative, but not limitative examples of alkoxycarbonyl are methoxycarbonyl, ethoxycarbonyl, t-butoxycarbonyl and the like.

The term "alkoxycarbonylalkyl", alone or in combination, describes an alkoxycarbonyl group, which is linked via an alkyl radical. Representative, but not limitative examples of alkoxycarbonylalkyl are methoxycarbonylpropyl, ethoxycarbonylbutyl, 2-t-butoxycarbonylethyl and the like.

The term "alkylcarbonyl", alone or in combination, describes an alkyl group, which is linked via a carbonyl group. Representative, but not limitative examples of alkylcarbonyl are acetyl, 1-oxopropyl, 2,2-dimethyl-1-oxopropyl, 1-oxobutyl, 1-oxopentyl and the like.

The term "alkylcarbonylalkyl", alone or in combination, describes an alkylcarbonyl group, which is linked via an alkyl group. Representative, but not limitative examples of alkylcarbonylalkyl are 2-oxopropyl, 3,3-dimethyl-2-oxopropyl, 3-oxobutyl, 3-oxopentyl and the like.

The term "alkylcarbonyloxy", alone or in combination, describes an alkylcarbonyl group, which is linked via an oxygen bridge. Representative, but not limitative examples of alkylcarbonyloxy are acetyloxy, ethylcarbonyloxy, t-butylcarbonyloxy and the like.

The term "Alkylsulphinyl", alone or in combination, describes an alkyl group, which is linked via a sulphinyl group. Representative, but not limitative examples of alkylsulphinyl are methylsulphinyl, ethylsulphinyl and the like.

The term "alkylsulphinylalkyl", alone or in combination, describes an alkylsulphinyl group, which is linked via an alkyl group. Representative, but not limitative examples of alkylsulphinylalkyl are methylsulphinylmethyl, ethylsulphinylmethyl and the like.

The term "alkylsulphonyl", alone or in combination, describes an alkyl group, which is linked via a sulphonyl group. Representative, but not limitative examples of alkylsulphonyl are methylsulphonyl, ethylsulphonyl and the like.

The term "alkylsulphonylalkyl", alone or in combination, describes an alkylsulphonyl group, which is linked via an alkyl group. Representative, but not limitative examples of alkylsulphonylalkyl are methylsulphonylmethyl, ethylsulphonylmethyl and the like.

The term "alkylthio", alone or in combination, describes an alkyl group, which is linked via a thiogroup. Representative, but not limitative examples of alkylthio are methylsulphanyl, ethylsulphanyl, t-butylsulphanyl, hexylsulphanyl and the like.

The term "alkylthioalkyl", alone or in combination, describes an alkylthio group, which is linked via an alkyl group. Representative, but not limitative examples of alkylthioalkyl are methylsulphanylmethyl, 2-(ethylsulphanyl)ethyl, and the like.

The term "amino", alone or in combination, describes an —$NR_eR_f$ group, in which $R_e$ and $R_f$ are chosen independently of each other from hydrogen, alkyl, aryl, arylalkyl, acyl, alkylcarbonyl, arylcarbonyl, carbamoyl, ureido, formyl, alkylsulphonyl, arylsulphonyl and the like.

The term "aminoalkyl", alone or in combination, describes an amino group, which is linked via an alkyl group. Representative, but not limitative examples of aminoalkyl are aminomethyl, 2-(amino)ethyl, benzyl-(methyl)aminomethyl, dimethylaminomethyl and the like.

The term "aminocarbonyl", alone or in combination, describes an aminogroup, which is linked via a carbonyl group. Representative, but not limitative examples of aminocarbonyl are dimethylaminocarbonyl, benzylaminocarbonyl, ethylaminocarbonyl and the like.

The term "aminocarbonylalkyl", alone or in combination, describes an aminocarbonyl group, which is linked via an alkyl group. Representative, but not limitative examples of aminocarbonylalkyl are 2-amino-2-oxoethyl, 2-(benzylamino)-2-oxoethyl, 2-(methylamino)-2-oxoethyl, 4-amino-4-oxobutyl, 4-(dimethylamino)-4-oxobutyl and the like.

The term "aryl", alone or in combination, describes an aromatic carbocyclic group containing at least one aromatic ring, for example phenyl or biphenyl, or condensed ring systems in which at least one ring is aromatic, for example 1,2,3,4-tetrahydronaphthyl, naphthyl, anthryl, phenanthryl, fluorenyl and the like. The aryl group can carry one or more substituents, which are chosen independently of each other from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphnyl, alkylsulphonylalkyl, alkylthio, alkylthioalkyl, alkinyl, amino, aminoalkyl, aminocarbonyl, aminocarbonylalkyl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro and the like.

The term "arylalkenyl", alone or in combination, describes an aryl group, which is linked via an alkenyl group. Representative, but not limitative examples of arylalkenyl are 2-phenylethenyl, 3-phenylpropen-2-yl, 2-naphth-2-ylethenyl and the like.

The term "arylalkoxy", alone or in combination, describes an aryl group, which is linked via an alkoxy group. Representative, but not limitative examples of arylalkoxy are 2-phenylethoxy, 5-phenylpentyloxy, 3-naphth-2-ylpropoxy and the like.

The term "arylalkyl", alone or in combination, describes an aryl group, which is linked via an alkyl group. The aryl group can be unsubstituted or substituted. Representative, but not limitative examples of arylalkyl are benzyl, 2-phenylethyl, 3-phenylpropyl, 2-naphth-2-ylethyl and the like.

The term "aryloxy", alone or in combination, describes an aryl group, which is linked via an oxy group. The aryl group can be unsubstituted or substituted. Representative, but not limitative examples of aryloxy are phenoxy, naphthyloxy, 3-bromphenoxy, 4-chlorphenoxy, 4-methylphenoxy, 3,4-dimethoxyphenoxy and the like.

The term "carbamoyl", alone or in combination, describes a —$C(O)NR_eR_f$ group.

The term "thiocarbamoyl", alone or in combination, describes a —$C(S)NR_eR_f$ group.

The term "carbonyl", alone or in combination, describes a —$C(O)$ group.

The term "carboxy", alone or in combination, describes a —$CO_2H$ group.

The term "carboxyalkyl", alone or in combination, describes a carboxy group, which is linked via an alkyl group. Representative, but not limitative examples of carboxyalkyl are carboxymethyl, 2-carboxyethyl, 3-carboxypropyl and the like.

The term "cyano", alone or in combination, describes a —C≡N group.

The term "cyanoalkyl", alone or in combination, describes a cyano group, which is linked via an alkyl group. Representative, but not limitative examples of cyanoalkyl are cyanomethyl, 2-cyanoethyl, 3-cyanopropyl and the like.

The term "cycloalkyl", alone or in combination, describes a saturated cyclic hydrocarbon radical with 3-15 carbon atoms, which can carry one or more substituents. The substituents are independently chosen from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkinyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro and the like. Representative, but not limitative examples of cycloalkyl are cyclopropyl, cyclobutyl, cyclopentyl, cyclohexyl, cycloheptyl and cyclooctyl. In polycyclic cycloalkyl radicals one of the fused rings can be aromatic, like for example 1-indanyl, 2-indanyl, tetrahydronaphthyl and the like.

The terms "cycloalkenyl" and "cycloalkinyl" describe cyclic hydrocarbon radicals, which contain at least one carbon-carbon double or triple bond. Like the cycloalkyl radicals, these radicals can carry one or more substituents.

The term "formyl", alone or in combination, describes a —C(O)H group.

The term "formylalkyl", alone or in combination, describes a formyl group, which is linked via an alkyl group. Representative, but not limitative examples of formylalkyl are formylmethyl, 2-formylethyl, and the like.

The terms "halo" or "halogen", alone or in combination, describe fluorine, bromine, chlorine, or iodine.

The term "haloalkyl", alone or in combination, describes an alkyl group, in which at least one hydrogen atom is replaced by halogen. Representative, but not limitative examples of haloalkyl are chloromethyl, 2-fluoroethyl, trifluoromethyl, pentafluoroethyl, 2-chloro-3-fluoropentyl and the like.

The term "haloalkoxy", alone or in combination, describes an alkoxy group, in which at least one hydrogen atom is replaced by halogen. Representative, but not limitative examples of haloalkoxy are chloromethoxy, 2-fluoroethoxy, trifluoromethoxy, pentafluoroethoxy and the like.

The term "heterocyclyl", alone or in combination, describes a monocyclic, bicyclic or polycylic ring system with up to 15 ring atoms, containing at least one heteroatom independently chosen from nitrogen, oxygen, or sulphur, the ring(s) being able to be saturated, partially unsaturated or unsaturated or aromatic. Representative, but not limitative, examples of heterocyclyl are furyl, imidazolyl, imidazolinyl, imidazolidinyl, isothiazolyl, isoxazolyl, morpholinyl, oxadiazolyl, oxazolyl, oxazolinyl, oxazolidinyl, piperazinyl, piperidinyl, pyranyl, pyrazinyl, pyrazolyl, pyridyl, pyrimidinyl, pyridazinyl, pyrrolyl, pyrrolinyl, pyrrolidinyl, tetrahydrofuranyl, tetrahydrothienyl, thiadiazolyl, thiazolyl, thiazolinyl, thiazolidinyl, thienyl, thiomorpholinyl, 1,1-dioxothiomorpholinyl, benzimidazolyl, benzothiazolyl, benzothienyl, benzoxazolyl, benzofuranyl, indolyl, indolinyl, isobenzofuranyl, isobenzothienyl, isoindolyl, isoindolinyl, isoquinolinyl, quinolinyl and the like. The heterocycle radicals can carry one or more substituents, these being independently chosen from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, cycloalkyl, formyl, formylalkyl, halogen, haloalkoxy, haloalkyl, heterocyclyl, heteroaryl, hydroxy, hydroxyalkyl, mercapto, nitro and the like.

The term "heteroaryl", alone or in combination, is a special case of heterocyclyl and describes a monocyclic, bicyclic or polycylic ring system, in which the or at least one ring is heteroaromatic.

The term "heterocyclylalkenyl", alone or in combination, describes a heterocyclyl group, which is linked via an alkenyl group. Representative, but not limitative examples of heterocyclylalkenyl are 2-pyrid-3-ylethenyl, 3-quinolin-3-ylpropen-2-yl, 5-pyrid-4-ylpentylen-4-yl and the like.

The term "heterocyclylalkoxy", alone or in combination, describes a heterocyclyl group, which is linked via an alkoxy group. Representative, but not limitative examples of heterocyclylalkoxy are 2-pyrid-3-ylethoxy, 3-quinolin-3-ylpropoxy, 5-pyrid-4-ylpentyloxy and the like.

The term "heterocyclylalkyl", alone or in combination, describes a heterocyclyl group, which is linked via an alkyl group. Representative, but not limitative examples of heterocyclylalkyl are 2-pyrid-3-ylmethyl, 2-pyrimidin-2-ylpropyl and the like.

The term "heterocyclyloxy", alone or in combination, describes a heterocyclyl group, which is linked via an oxygen bridge. Representative, but not limitative examples of heterocyclyloxy are pyrid-3-yloxy, quinolin-3-yloxy and the like.

The terms "hydroxy" or "hydroxyl", alone or in combination, describe an —OH group.

The term "hydroxyalkyl", alone or in combination, describes an alkyl group, in which at least one hydrogen atom is replaced by a hydroxyl group. Representative, but not limitative examples of hydroxyalkyl are hydroxymethyl, 2-hydroxyethyl, 3-hydroxypropyl, 2-ethyl-4-hydroxyheptyl and the like.

The term "nitro", alone or in combination, describes an —NO$_2$ group.

The term "oxo", alone or in combination, describes an =O group.

The term "oxy", alone or in combination, describes an —O— group.

The terms "mercapto" and "thiol" describe a —SH group.

The terms "thio", "sulphinyl" and "sulphonyl" describe an —S(O)$_n$ group with n=0, 1 or 2.

The compounds of Formula I according to the invention can be present in free form, as pharmaceutically acceptable acid addition salts, as pharmaceutically acceptable salts of acid compounds of Formula I with bases, as pharmaceutically acceptable esters of hydroxy or carboxy group-containing compounds of Formula I and as hydrates or solvates thereof. The term "pharmaceutically acceptable salts" refers to salts which do not reduce the biological effect and properties of the free bases and which are not biologically or otherwise undesirable.

The acid addition salts are formed from the free bases using inorganic acids, such as hydrochloric acid, hydrobromic acid, sulphuric acid, nitric acid, phosphoric acid and the like, preferably hydrochloric acid or hydrobromic acid, or using organic acids, such as acetic acid, propionic acid, glycolic acid, pyruvic acid, oxalic acid, maleic acid, malonic acid, succinic acid, tartaric acid, salicylic acid, citric acid, benzoic acid, mandelic acid, methanesulphonic acid, p-toluenesulphonic acid and the like. If certain compounds of Formula I are prepared by the cycloaddition of bis-guanidine carbonate described below they can form as carbonates.

Compounds of Formula I which contain acid groups can form salts with inorganic bases or with organic bases. Preferred salts with inorganic bases are, but not exclusively, sodium, potassium, lithium, ammonium, calcium, magnesium salts and the like. Preferred salts with organic bases are, but not exclusively, salts with primary, secondary and tertiary, optionally substituted amines including all naturally occurring substituted amines, with cyclic amines and with basic ion-exchange resins, such as isopropylamine, trimethylamine, diethylamine, triethylamine, tripropylamine, ethanolamine, lysine, arginine, N-ethylpiperidine, piperidine, polyamine resins and the like. Compounds of Formula I which contain an acid group can also be present as zwitterions.

The invention also comprises pharmaceutically acceptable esters of hydroxy or carboxy group-containing compounds of Formula I. "Pharmaceutically acceptable esters" means that in compounds of Formula I corresponding functional groups are derivated to ester groups in such a way that they are transformed back to their active form again in vivo. On the one hand COOH groups can be esterified. Examples of suitable esters of this type are alkyl and aralkylesters. Preferred esters of this type are methyl, ethyl, propyl, butyl and benzylesters and (R/S)-1-[(isopropoxycarbonyl)oxy]ethyl esters. Ethyl esters and the isomeric butylesters are particularly preferred. On the other hand OH-groups can be esterified. Examples of such compounds contain physiologically acceptable and metabolically labile ester groups, such as methoxymethyl esters, methylthiomethyl esters, pivaloyloxymethyl esters and similar ester groups.

Compounds of Formula I were examined in the following test for their affinity to the NPFF receptors:

Hamster cells suitable for neuropeptide FF receptor-binding studies (Chinese Hamster Ovary cells, CHOSP10) which in each case produce the NPFF1 or NPFF2 receptor, were multiplied in standard cell-culture conditions. The cell-culture medium was sucked out and 5 ml of buffer A (5 mM Tris pH=7.4, 1 mM $MgCl_2$) added per 17 cm Petri dish. The cells were scraped off the cell-culture plate and transferred into a 50 ml Falcon vessel. The cells were then centrifuged for 5 minutes at 450 g, resuspended in buffer A once again and mixed for 30 seconds on a Polytron Vortexer. After centrifugation at 30,000 g for 20 minutes the supernatant was discarded and the membrane pellet taken up in 500 µl buffer C (75 mM Tris pH=7.4, 25 mM $MgCl_2$, 250 mM sucrose, 0.1 mM PMSF, 0.1 mM phenanthroline). The membrane-buffer mixture was then divided into aliquots and deep-frozen. The protein content of an aliquot was determined by the Lowry method.

The binding test was carried out in a final volume of 250 µl. 100 µl membrane-buffer mixture corresponding to 35 µg protein content was mixed with 95 µl binding buffer (50 mM Tris pH 7.4, 60 mM NaCl, 0.1% protease-free BSA, 0.01% $NaN_3$). After addition of 5 µl of a concentration of test substance per measurement point in each case, 0.2 nM $^{125}$I-Tyr1-NPFF (NEN, NEX381) per measurement point was added in 50 µl. After 90 minutes' incubation at room temperature the samples were sucked out through a GF/C filter (Millipore (MAHFC1H60)) and the filter was washed with ice cold binding buffer with 3 times 300 µl (Packard Filtermate). After addition of 55 µl Microscint 40 (Packard 6013641) scintillation fluid the measurement points were quantified in the gamma counter (Packard, Top Count NXT).

Non-specific binding was ascertained in the presence of 1 µM unmarked neuropeptide FF. Specific binding is defined as the difference between total and non-specific binding. $IC_{50}$ values are defined as that concentration of the antagonist which displaces 50% of the $^{125}$I-marked neuropeptide FF. This concentration is ascertained by linear regression analysis after logit/log-transformation of the binding values.

Preferred compounds according to the invention show, in the receptor binding study described above, $IC_{50}$ values below 1000 nM, particularly preferred compounds show $IC_{50}$ values below 100 nM, quite particularly preferred ones, below 10 nM.

The results of the representative compounds of Formula I studied in the biological test described above are summarized in Table 1 below.

TABLE 1

NPFF1 receptor binding

| Compound | Binding NPFF1 $IC_{50}$ [nM] |
| --- | --- |
| rac-N-(4-methyl-6-propyl-5,6,7,8-tetrahydro-quinazolin-2-yl)-guanidine | 1 |
| rac-N-(6-isopropyl-4-methyl-5,6,7,8-tetrahydro-quinazolin-2-yl)-guanidine | 2 |
| rac-N-(4-methyl-5,6,7,8-tetrahydro-quinazolin-2-yl)-guanidine | 4 |
| rac-N-(4,5-dimethyl-5,6,7,8-tetrahydro-quinazolin-2-yl)-guanidine | 7 |
| rac-N-(6-tert-butyl-4-methyl-5,6,7,8-tetrahydro-quinazolin-2-yl)-guanidine | 8 |
| rac-N-(4-methyl-8-phenyl-5,6,7,8-tetrahydro-quinazolin-2-yl)-guanidine | 16 |
| rac-N-(4-methyl-6-phenyl-5,6,7,8-tetrahydro-quinazolin-2-yl)-guanidine | 16 |
| rac-N-[6-(1,1-dimethyl-propyl)-4-methyl-5,6,7,8-tetrahydro-quinazolin-2-yl]-guanidine | 19 |
| rac-N-(8-tert-butyl-4-methyl-5,6,7,8-tetrahydro-quinazolin-2-yl)-guanidine | 39 |
| rac-N-(4,6-dimethyl-5,6,7,8-tetrahydro-quinazolin-2-yl)-guanidine | 48 |
| rac-N-(4-methyl-6,7,8,9-tetrahydro-5H-cycloheptapyrimidin-2-yl)-guanidine | 54 |
| rac-N-(4-methyl-5,6,7,8,9,10-hexahydro-cyclooctapyrimidin-2-yl)-guanidine | 60 |
| rac-N-(8-sec-butyl-4-methyl-5,6,7,8-tetrahydro-quinazolin-2-yl)-guanidine | 73 |

As mentioned at the outset, the compounds according to the invention, because of their capacity to block the neuropeptide FF receptors, are valuable in the treatment of pain, hypersensitivity to pain (hyperalgesia) and chronic, acute, long-lasting or temporary pain, which pain can be of operative, traumatic, or pathological origin. Above all they supplement the current treatment methods for chronic pain with the advantage of preventing or curing undesirable opioid tolerance and/or dependence. The substances according to the invention are also suitable for the treatment of withdrawal symptoms in the case of alcohol, psychotropics and nicotine dependences and for the prevention or elimination of these dependences. The compounds can additionally be used for the regulation of insulin secretion, food intake, memory functions, blood pressure, and of the electrolyte and energy balance and for the treatment of incontinence.

The compounds according to the invention can be transformed into suitable galenic dosage forms using methods which are generally known and familiar to every person skilled in the art. Such dosage forms are for example tablets, coated tablets, dragees, capsules, injection solutions etc. Suitable excipients and adjuvants for the preparation of such galenic dosage forms are also generally known and familiar to every person skilled in the art. In addition to one or more of the compounds according to the invention these dosage forms can also contain further pharmacologically active compounds.

The dosage of the compounds according to the invention or of the dosage forms containing them is to be matched by the doctor in attendance to the respective needs of the patient. In general a daily dose of 0.1-20 mg, preferably 0.5-5 mg of a compound according to the invention per kg body weight of the patient should be appropriate.

The guanidine derivatives of general Formula I according to the invention, and the corresponding starting and intermediate products, can be prepared using methods known in organic synthesis and isolated and purified using known techniques such as precipitation, chromatography, crystallization, preparative reversed-phase HPLC, etc. Stereoisomer mixtures which may be obtained, such as racemates, can be separated by generally customary methods, preferably by chiral-phase chromatography.

In a general way, bicyclic guanidine group containing compounds of Formula I can be prepared according to the following Diagram 1:

the compound obtained, optionally this/these nitrogen atom(s) is/are correspondingly substituted with an agent releasing a radical R' and optionally an obtained basic compound is converted into a pharmaceutically acceptable salt with an acid, or an obtained basic compound, containing an acid group, into a pharmaceutically acceptable salt with a base, or an obtained hydroxy or carboxy group-containing compound into a pharmaceutically acceptable ester and optionally the obtained product is converted into a hydrate or solvate.

Thus bicyclic pyrimidine derivatives of Formula IV, which represent a sub-group of the compounds of Formula I, can be prepared according to the following Diagram 2:

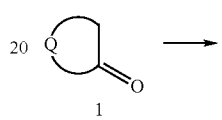

Diagram 2

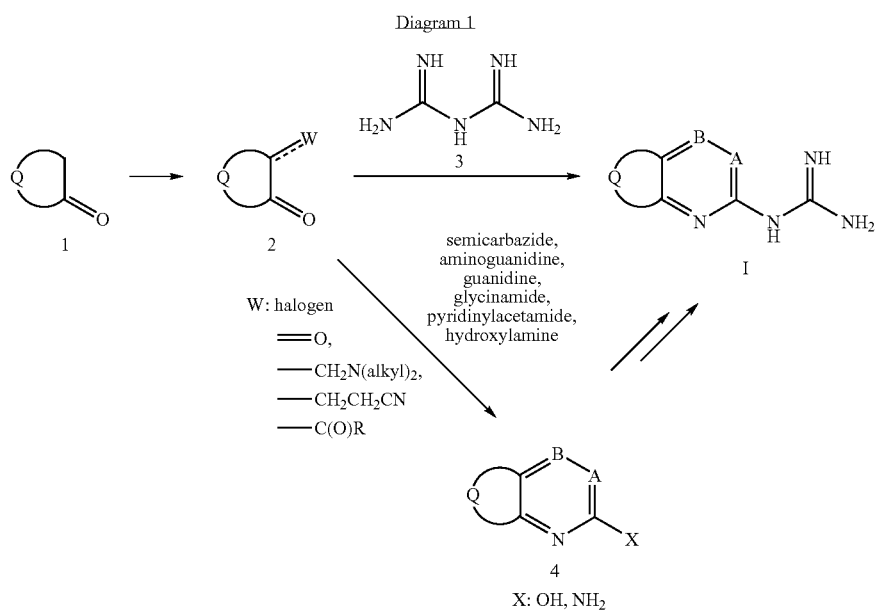

A compound of Formula 1, in which the nitrogen atom(s) which may be present in Q is/are protected, or correspondingly substituted with a radical R'-releasing agent, is activated in α-position to form the carbonyl group with a function W according to known methods, e.g. acylated, formylated, alkylated, aminoalkylated, halogenated, or oxidized, whereupon the obtained compound of Formula 2 is subjected to a cyclo-condensation with a nitrogen-containing reagent, such as bis-guanidine of Formula 3, semicarbazide, aminoguanidine, guanidine, glycinamide, pyridinylacetamide or hydroxylamine, optionally the obtained compound of Formula 4 is converted, using known methods, into the target compound of Formula I, optionally the protective group(s) located on the nitrogen atom(s) which may be present is/are split off from -continued

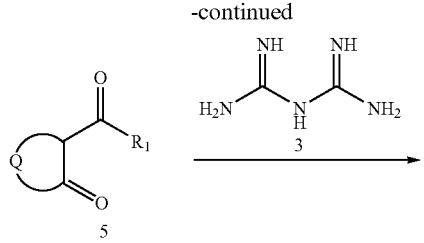

-continued

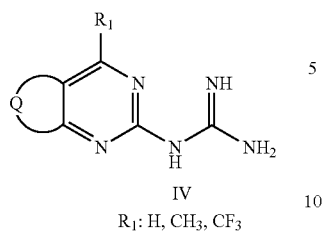

IV
R₁: H, CH₃, CF₃

Cycloalkanones of Formula 1 can be acylated by known methods in α-position to form the carbonyl group (J. Med. Chem. 1989, 32(2), 351-357) or formylated (e.g. J. Org. Chem. 2000, 65, 7145-7150). The following cyclocondensation of 1,3-dioxo compounds (5) with bis-guanidine (3) takes place in known manner and leads to the desired 2-guanidine derivatives of Formula IV (Org. Lett. 2001, 3(24), 3887-3889). Generally, heterocyclic oxo compounds of Formula I can also be converted analogously to the corresponding target compounds of Formula IV. It is to be borne in mind that an —NH-group present in Q of the starting product is to be provided with a common protective group.

The bicyclic pyridine derivatives of Formula V, which also represent a sub-group of the compounds of Formula I darstellen, can be prepared according to the following Diagram 3.

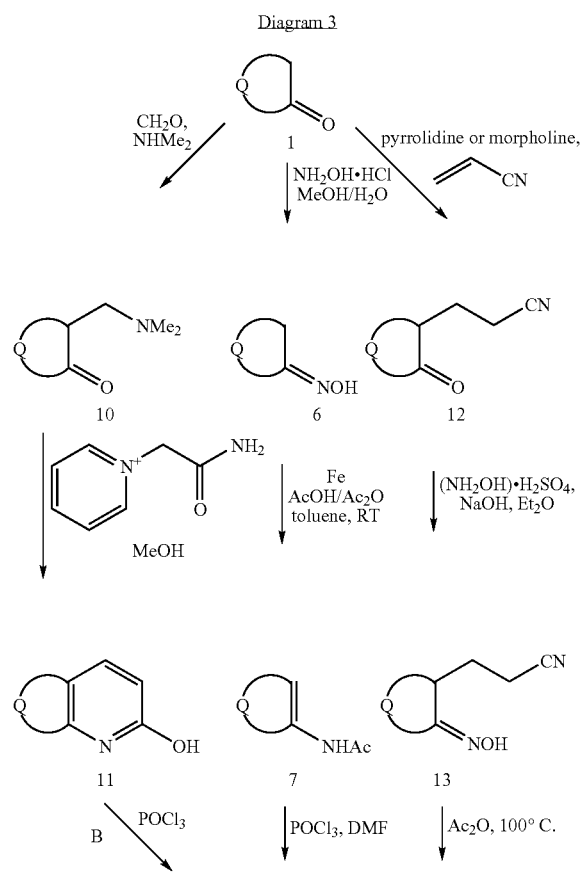

-continued

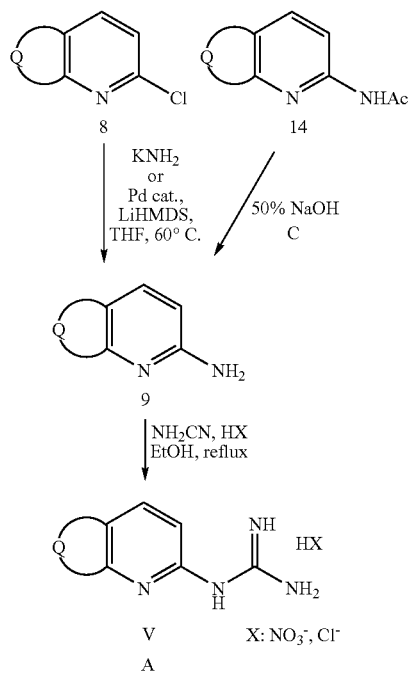

The compound of Formula 9 can be obtained starting from cyclic ketone of Formula 1 in various multi-stage syntheses A (J. Chem. Soc. Perkin. Trans. I, 1984, 1173), B (Chem. Ber. 1957, 90, 711-20), or C (J. Org. Chem. 1993, 58 (4), 887-891). It can then be transformed for example using cyanamide (NH₂CN), in the presence of an acid such as for example hydrochloric acid or nitric acid, into the desired guanidinopyridine of Formula V.

The bicyclic pyrazine derivatives of Formula VI, which represent another sub-group of compounds of Formula I, can be prepared according to Diagram 4 according to known methods.

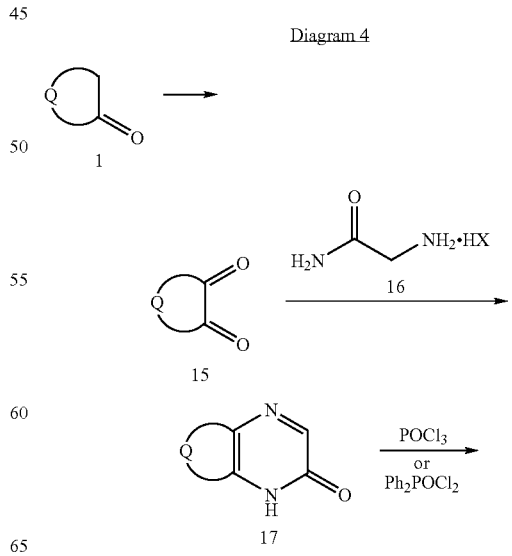

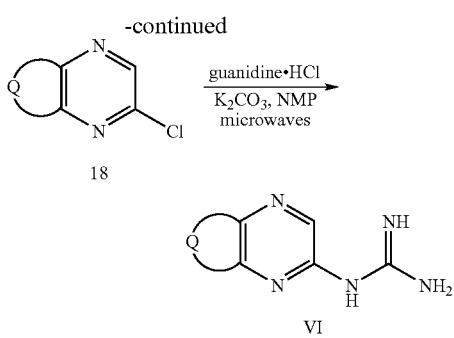

The cyclic ketones of Formula 1 are converted into the corresponding diketones of Formula 15, which are subsequently reacted with glycinamide of Formula 16 in the presence of a suitable base (U.S. Pat. No. 3,505,327; 7 Apr. 1970). The thus obtained compounds of Formula 17 are converted with a suitable halogenation agent into the corresponding halogen derivative, preferably into the chlorine compound of Formula 18 (Heterocycles 1989, 28(2), 783-789). Substitution in the presence of a suitable base produces the desired end-product of Formula VI.

The bicyclic triazine derivatives of Formula VII, which represent another sub-group of the compounds of Formula I, can also be prepared starting from cyclic diketone of Formula 15 according to the following Diagram 5.

guanidine and a suitable base to form the desired guanidino-triazine of Formula VII. Alternatively the cyclic diketone 15 can be converted using aminoguanidine into a 2-amino-triazine derivative of Formula 22, which then produces the desired end-product VII by means of known guanylation methods, preferably by reaction with cyanamide. A 2-amino-triazine derivative of Formula 22 can also be obtained by converting a halo compound of Formula 21 with potassium amide or ammonia.

The preparation of compounds of Formula III according to the invention preferably occurs according to the following Diagram 6.

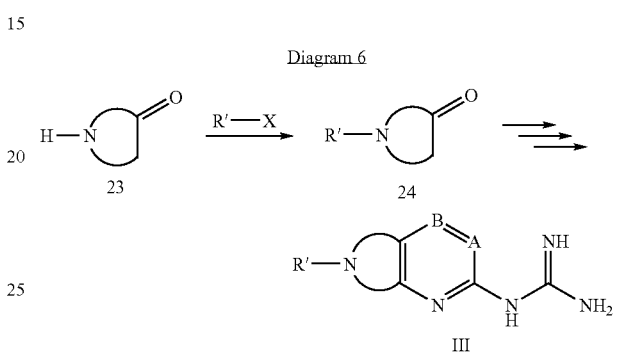

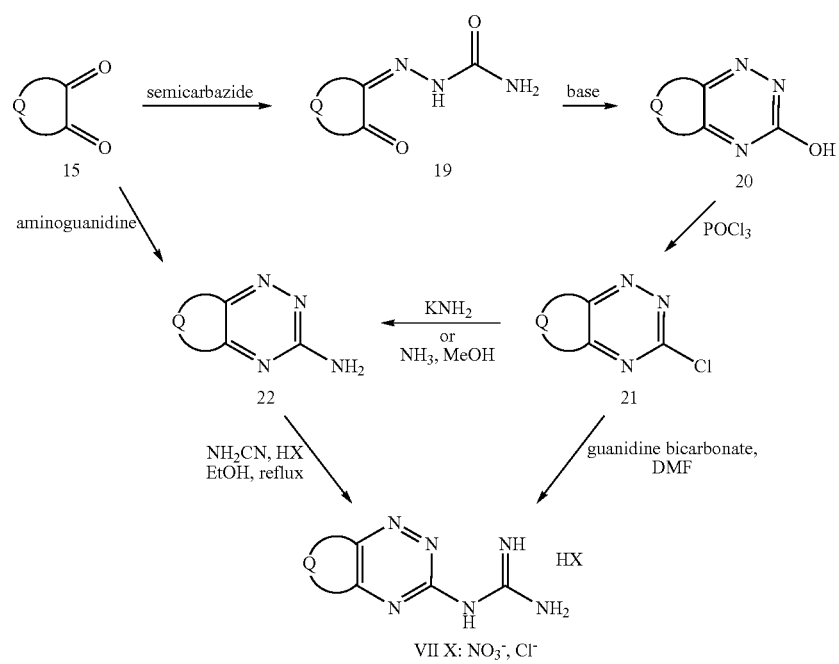

The diketone of Formula 15 is converted, according to known methods, by reaction with semicarbazide into monosemicarbazone of Formula 19, which after cyclization in the presence of a suitable base produces the corresponding hydroxytriazine of Formula 20. Halogenation, preferably chlorination, with a suitable halogenation agent produces the halogen compound of Formula 21, which is converted using Starting from the cyclic azaketone of Formula 23 the R'-radicals defined at the outset are converted, under known conditions using the respective corresponding R'-releasing reagents, such as e.g. alkylhalides, carboxylic acid halides or anhydrides, or also carboxylic acids in the presence of coupling reagents and with a base as auxiliary reagent, with chloroformates, sulphonyl halides, isocyanates, isothiocyanates and the like, to the corresponding compound of Formula 24, which is then converted under the conditions specified in Diagrams 2-5 into the target compound of Formula III.

The cyclic azaketones of Formula 23 which are required as starting products can be prepared according to methods known from the literature (Yokoo et al., Bull. Chem. Soc. Japan 1959, 29, 631; Griss et al., DE 2206385, published 10 Feb. 1972).

Typically the synthesis both of the guanidine derivatives of general Formula I according to the invention and of the corresponding intermediate products is carried out in solution using an organic solvent. The introduction and removal of protective groups takes place with typical methods known to a person skilled in the art (T. W. Greene & P. G. M. Wuts in Protective Groups in Organic Synthesis, Third Edition, John Wiley & Sons, 1999).

Suitable organic solvents are those which behave inertly under the chosen reaction conditions. These are preferably ethers, such as diethyl ether, dioxane, tetrahydrofuran or glycoldimethylether; or alcohols, such as for example methanol, ethanol, propanol, isopropanol, butanol, isobutanol or tert-butanol; or hydrocarbons, such as benzene, toluene, xylene, hexane, cyclohexane or petroleum fractions; or halogenated hydrocarbons, such as dichloromethane, trichloromethane, tetrachloromethane, dichloroethylene, trichloroethylene or chlorobenzene; or also ethyl acetate, triethylamine, pyridine, dimethylsulphoxide, dimethylformamide, hexamethylphosphoramide, acetonitrile, acetone or nitromethane. Mixtures of the solvents mentioned can also be used.

Bases which can be used for the described processes, are generally inorganic or organic bases. Preferred are alkali hydroxides, for example sodium or potassium hydroxide, alkaline-earth metal hydroxides, for example barium hydroxide, alkali carbonates such as sodium carbonate or potassium carbonate, alkaline-earth metal carbonates, such as calcium carbonate, or alkali or alkaline-earth metal alkoxides such as sodium or potassium methoxide, sodium or potassium ethoxide or potassium-tert-butoxide, or organic amines, e.g. trialkyl-($C_1$-$C_6$)-amines, such as triethylamine, or heterocyclic amines, such as 1,4-diazabicyclo[2.2.2]octane (DABCO), 1,8-diazabicyclo[5.4.0]undec-7-ene (DBU), pyridine, 4-dimethylaminopyridine, N-methyl-piperidine or N-methylmorpholine. It is also possible to use alkali metals, such as sodium, or its hydrides, such as sodium hydride. The bases mentioned can, where expedient, be used as an acid-binding auxiliary.

Dehydrating reagents, for example carbodiimides, such as diisopropylcarbodiimide, dicyclohexylcarbodiimide or N-(3-dimethylaminopropyl)-N'-ethylcarbodiimide-hydrochloride, or carbonyl compounds, such as carbonyldiimidazole, or 1,2-oxazolium compounds, such as 2-ethyl-5-phenyl-isoxazolium-3-sulphonate, or also propane phosphonic acid anhydride or isobutyl chloroformate or benzotriazolyloxytris-(dimethylamino)phosphonium-hexafluorophosphate (BOP) or diphenylphosphoramidate or methanesulphonyl chloride, can serve as coupling reagents, if expedient in the presence of bases, such as triethylamine or N-ethylmorpholine or N-methylpiperidine or diisopropylethylamine.

The examples below serve to explain the present invention, but in no way limit it.

EXAMPLE 1

N-(4-methyl-5,6,7,8-tetrahydro-quinazolin-2-yl)-guanidine-carbonate 2-acetylcyclohexanone (500 μmol, Aldrich) together with bis-guanidine 3 (1 mmol) and potassium carbonate (2.5 mmol) was introduced into EtOH (2 ml) and converted a) in a microwave oven (10 min, 120° C.) or b) at 80° C. overnight. When the reaction was complete the reaction mixture was mixed with water, until all the carbonate had dissolved, and the product which precipitated overnight was filtered off. $t_R$ 1.39; MS (pos. Ion.) m/z 206.37 [M+H]$^+$.

Bis-guanidine-carbonate 3 (Reagent for Example 1)

A mixture of dicyandiamide (476 mmol), ammonium chloride (12 mol) and phenol (120 g) was heated for 6 hours to 120-140° C. For processing the reaction mixture was introduced into water (500 ml) and in order to remove the phenol it was extracted several times with diethyl ether. The product was precipitated by addition of saturated potassium carbonate solution and filtered off. After recrystallization from methanol 3 is obtained in the carbonate salt form as an almost colourless solid. (Org. Lett. 2001, 3(24), 3887-3889).

Analogously to the preparation of Example 1, the compounds according to Examples 2 to 26 in Table 2 are prepared starting from the corresponding cyclic α-acylketones. In cases where the product did not crystallize out, a chromatographic purification was carried out on silica gel (Eluent: ethyl acetate/acetone/water/acetic acid 16:2:1:1) and the product was correspondingly isolated as acetate. Both the carbonates and the acetates could be converted, by dissolution in methanolic HCl and subsequent removal of the solvent in a vacuum, into the corresponding HCl salts.

Table 2 shows, for the products according to Examples 1-26, the structural formulae (including the acids from which the anions of the obtained salts are derived), the names of the corresponding bases and their empirical formulae and molecular weights and the starting products used for the preparation as well as physical data. All of the products are racemates.

The cyclic α-acylketones used are commercially available or were produced by acylation starting from the corresponding cycloalkanone according to methods known from the literature (J. Med. Chem. 1989, 32(2), 351-357; J. Org. Chem. 2000, 65(21), 7145-7150; J. Med. Chem. 1971, 14(10), 997-998). Examples of methods are described below for the various classes of compounds.

rac-2-acetyl-4-phenyl-cyclohexanone (Starting Product for Example 3)

A solution of 4-phenylcyclohexanone (10 mmol, Lancaster) in benzene (5 ml) is added dropwise to a suspension of NaH (20 mmol) in absolute ethyl acetate (20 mmol) and the reaction mixture is stirred after complete evolution of the gas for 3 h at 40° C. Then it is mixed with water, the reaction mixture is extracted three times with ether, the combined organic phases are washed with water and saturated sodium chloride solution, dried over sodium sulphate and the solvent is removed in a vacuum. After column chromatography purification on silica gel with hexane/EtOAc 15:1 a clean product is obtained. $t_R$ 2.14; MS (pos. Ion.) m/z 217.26 [M+H]$^+$. (J. Med. Chem. 1989, 32(2), 351-357).

The starting products for Examples 4-18 in Table 2 were also produced in a similar way and converted without chromatographic purification as crude products according to the method described for Example 1.

rac-3-acetyl-4-oxo-piperidine-1-carboxylic acid tert-butyl ester (Starting Product for Example 19)

A solution of 4-oxo-piperidine-1-carboxylic acid tert-butyl ester (2.5 mmol) in absolute THF (1 ml) was added at −78° C.

to a freshly prepared solution of LDA (2.76 mmol) in absolute THF (2 ml) and was stirred at this temperature for 2 h. Then acetylimidazole (2.76 mmol) dissolved in THF (1.5 ml) was added dropwise and the reaction mixture was stirred overnight, with warming to room temperature. The addition of saturated ammonium chloride solution was followed by extraction three times with ether, the combined organic phases were washed with water and saturated sodium chloride solution, dried over sodium sulphate and the solvent was removed in a vacuum. After column chromatography purification on silica gel with hexane/EtOAc 5:1 the product is obtained as a yellow oil. $t_R$ 2.09; MS (neg. Ion.) m/z 240.41 [M−H]⁻. (J. Med. Chem. 1989, 32(2), 351-357).

The conversion to the guanidine derivative took place in the same way as described for Example 1.

rac-5-isopropyl-2-oxo-cyclohexanecarbaldehyde (Starting Product for Example 20)

A solution of ethyl formate (6 mmol) in diethyl ether (2 ml) was added dropwise to a suspension of sodium methoxide (6 mmol) and 4-isopropyl-cyclohexanone (3 mmol) in absolute diethyl ether (3 ml) and after complete evolution of the gas the reaction mixture was stirred overnight at room temperature. The solid formed was filtered off, washed with diethyl ether and dried in a high vacuum. The product was obtained as a slightly yellow solid. $t_R$ 2.26; MS (pos. Ion.) m/z 169.32 [M+H]⁺. (J. Org. Chem. 2000, 65(21), 7145-7150).

The starting products for Examples 21-23 in Table 2 were also prepared in a similar way and converted according to the method described for Example 1.

rac-4-tert-butyl-2-(2,2,2-trifluoro-acetyl)-cyclohexanone (Starting Product for Example 24)

A solution of ethyl trifluoroacetate (6 mmol) in diethyl ether (2 ml) was added dropwise to a suspension of sodium methoxide (6 mmol) and 4-tert-butyl-cyclohexanone (3 mmol) in absolute diethyl ether (3 ml) and after complete evolution of the gas the reaction mixture was stirred overnight at room temperature. After being mixed with water, the reaction mixture was extracted three times with ether, the combined organic phases were washed with water and saturated sodium chloride solution, dried over sodium sulphate and the solvent was removed in a vacuum. The yellow oil thus obtained was converted as a crude product without further purification according to the method described for Example 1 with bis-guanidine carbonate. (J. Med. Chem. 1971, 14(10), 997-998).

The starting products for Examples 25 and 26 in Table 2 were prepared in a similar way and converted as crude products without chromatographic purification according to the method described for Example 1.

Analytical Methods

The compounds produced were analyzed using reverse-phase HPLC (Retention time $t_R$) on a Waters Alliance LC, equipped with a MassLynx-NT mass spectrometer on a GROM-SIL 120 ODS-4 HE HPLC column (particle size 3 μm, column length 30 mm, diameter 2 mm) with a linear gradient with water/0.06% formic acid (A) and acetonitrile/0.06% formic acid (B) of 5% to 95% B in 3 min. with a flow rate of 0.3 ml/min.

TABLE 2

Analytical data of the products of Examples 1-26

| Ex. | Structure | Name | Empirical formula Molecular weight | Starting product | $t_R$ [min] | MS data m/z [M + H]⁺ |
|---|---|---|---|---|---|---|
| 1 | 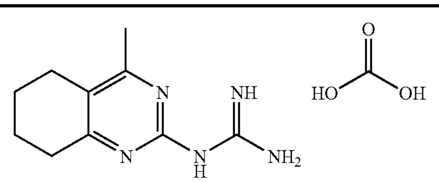 | N-(4-methyl-5,6,7,8-tetrahydro-quinazolin-2-yl)-guanidine | C10H15N5 205.3 | cyclo-hexanone | 1.39 | 206.3 |
| 2 | 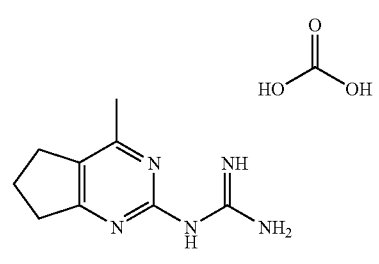 | N-(4-methyl-6,7-dihydro-5H-cyclopentapyrimidin-2-yl)-guanidine | C9H13N5 191.2 | cyclo-pentanone | 1.27 | 192.33 |
| 3 | 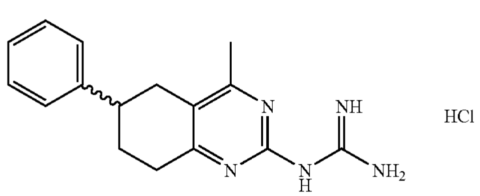 | N-(4-methyl-6-phenyl-5,6,7,8-tetrahydro-quinazolin-2-yl)-guanidine | C16H19N5 281.4 | 4-phenyl-cyclo-hexanone | 1.49 | 282.34 |

TABLE 2-continued

Analytical data of the products of Examples 1-26

| Ex. | Structure | Name | Empirical formula Molecular weight | Starting product | $t_R$ [min] | MS data m/z $[M + H]^+$ |
|---|---|---|---|---|---|---|
| 4 | 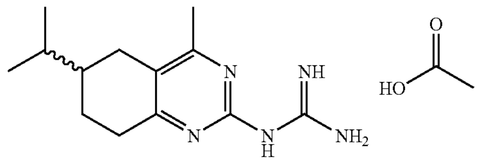 | N-(6-isopropyl-4-methyl-5,6,7,8-tetrahydro-quinazolin-2-yl)-guanidine | C13H21N5 247.3 | 4-isopropyl-cyclo-hexanone | 1.52 | 248.53 |
| 5 | 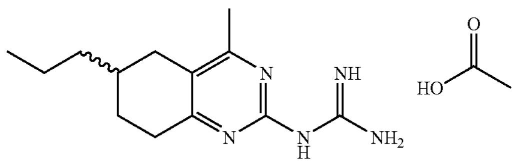 | N-(4-methyl-6-propyl-5,6,7,8-tetrahydro-quinazolin-2-yl)-guanidine | C13H21N5 247.3 | 4-n-propyl-cyclo-hexanone | 1.57 | 248.59 |
| 6 | 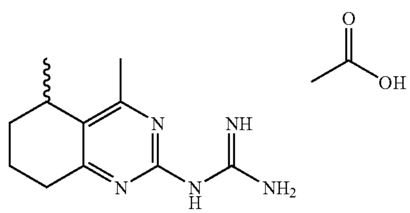 | N-(4,5-dimethyl-5,6,7,8-tetrahydro-quinazolin-2-yl)-guanidine | C11H17N5 219.3 | 3-methyl-cyclo-hexanone | 1.38 | 220.28 |
| 7 | 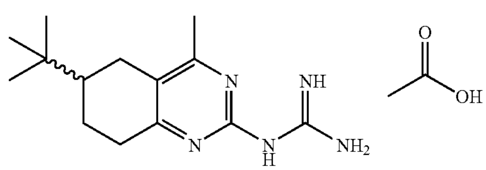 | N-(6-tert-butyl-4-methyl-5,6,7,8-tetrahydro-quinazolin-2-yl)-guanidine | C14H23N5 261.4 | 4-tert-butyl-cyclo-hexanone | 1.63 | 262.33 |
| 8 | 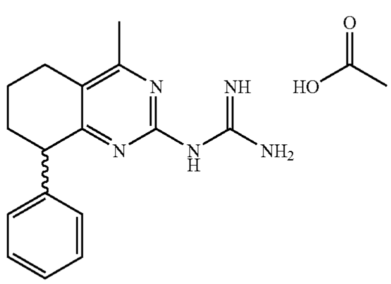 | N-(4-methyl-8-phenyl-5,6,7,8-tetrahydro-quinazolin-2-yl)-guanidine | C16H19N5 281.4 | 2-phenyl-cyclo-hexanone | 1.48 | 282.34 |
| 9 | 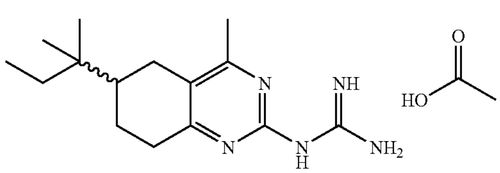 | N-[6-(1,1-dimethyl-propyl)-4-methyl-5,6,7,8-tetrahydro-quinazolin-2-yl]-guanidine | C15H25N5 275.4 | 4-tert-amyl-cyclo-hexanone | 1.68 | 276.62 |
| 10 | 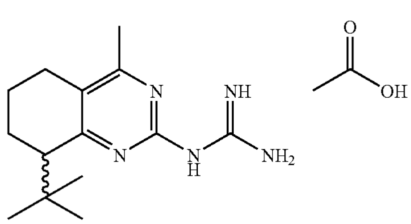 | N-(8-tert-butyl-4-methyl-5,6,7,8-tetrahydro-quinazolin-2-yl)-guanidine | C14H23N5 261.4 | 2-tert-butyl-cyclo-hexanone | 1.58 | 262.33 |

TABLE 2-continued

Analytical data of the products of Examples 1-26

| Ex. | Structure | Name | Empirical formula Molecular weight | Starting product | $t_R$ [min] | MS data m/z $[M + H]^+$ |
|---|---|---|---|---|---|---|
| 11 | 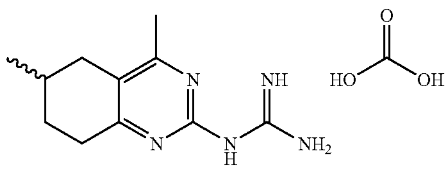 | N-(4,6-dimethyl-5,6,7,8-tetrahydro-quinazolin-2-yl)-guanidine | C11H17H5 219.3 | 4-methyl-cyclo-hexanone | 1.36 | 220.43 |
| 12 | 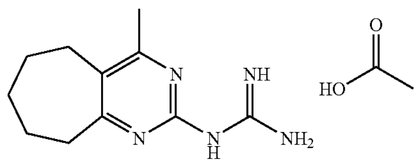 | N-(4-methyl-6,7,8,9-tetrahydro-5H-cycloheptapyrimidin-2-yl)-guanidine | C11H17N5 219.3 | cyclo-heptanone | 1.36 | 220.37 |
| 13 | 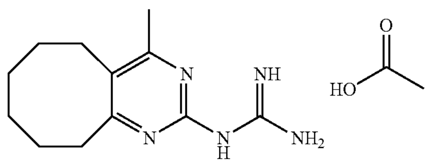 | N-(4-methyl-5,6,7,8,9,10-hexahydro-cyclooctapyrimidin-2-yl)-guanidine | C12H19N5 233.3 | cyclo-octanone | 1.39 | 234.54 |
| 14 | 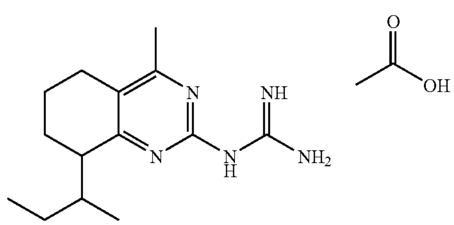 | N-(8-sec-butyl-4-methyl-5,6,7,8-tetrahydro-quinazolin-2-yl)-guanidine | C14H23N5 261.4 | 2-sec-butyl-cyclo-hexanone | 1.5 | 262.4 |
| 15 | 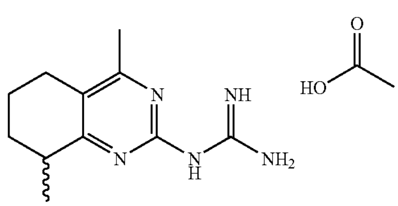 | N-(4,8-dimethyl-5,6,7,8-tetrahydro-quinazolin-2-yl)-guanidine | C11H17N5 219.3 | 2-methyl-cyclo-hexanone | 1.33 | 220.4 |
| 16 | 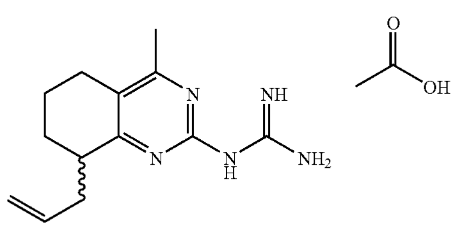 | N-(8-allyl-4-methyl-5,6,7,8-tetrahydro-quinazolin-2-yl)-guanidine | C13H19N5 245.3 | 2-allyl-cyclo-hexanone | 1.4 | 246.37 |
| 17 | 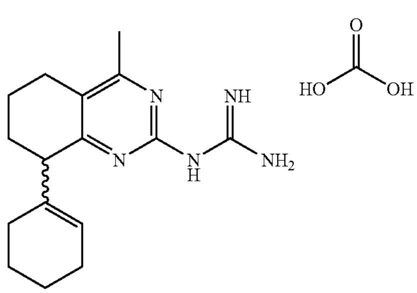 | N-(8-cyclohex-1-enyl-4-methyl-5,6,7,8-tetrahydro-quinazolin-2-yl)-guanidine | C16H23N5 285.4 | 2-(1-cyclo-hexenyl)-cyclo-hexanone | 1.61 | 286.38 |

TABLE 2-continued

Analytical data of the products of Examples 1-26

| Ex. | Structure | Name | Empirical formula Molecular weight | Starting product | $t_R$ [min] | MS data m/z $[M + H]^+$ |
|---|---|---|---|---|---|---|
| 18 | 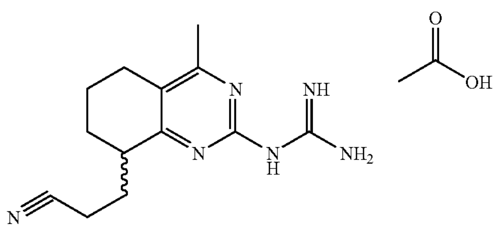 | N-[8-(2-cyano-ethyl)-4-methyl-5,6,7,8-tetrahydro-quinazolin-2-yl]-guanidine | C13H18N6 258.3 | 2-oxo-1-cyclohexane-propionitrile | 1.33 | 259.26 |
| 19 | 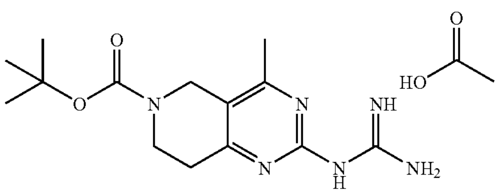 | 2-guanidino-4-methyl-7,8-dihydro-5H-pyrido[4,3-d]pyrimidin-6-carboxylic acid tert-butyl ester | C14H22N6O2 306.4 | 4-oxo-piperidine-1-carboxylic acid tert-butyl ester | 1.47 | 307.35 |
| 20 | 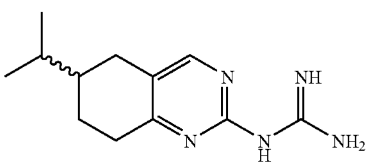 | N-(6-isopropyl-5,6,7,8-tetrahydro-quinazolin-2-yl)-guanidine | C12H19N5 233.3 | 4-isopropyl-cyclo-hexanone | 1.56 | 234.44 |
| 21 | 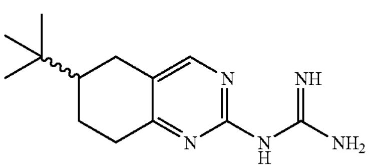 | N-(6-tert-butyl-5,6,7,8-tetrahydro-quinazolin-2-yl)-guanidine | C13H21N5 247.4 | 4-tert-butyl-cyclo-hexanone | 1.62 | 248.49 |
| 22 | 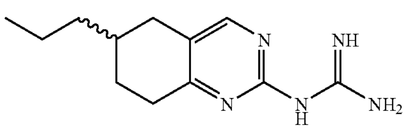 | N-(6-propyl-5,6,7,8-tetrahydro-quinazolin-2-yl)-guanidine | C12H19N5 233.3 | 4-n-propyl cyclo-hexanone | 1.57 | 234.38 |
| 23 | 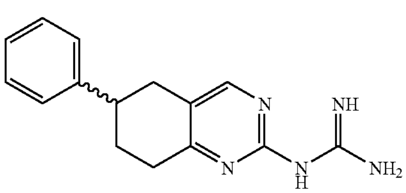 | N-(6-phenyl-5,6,7,8-tetrahydro-quinazolin-2-yl)-guanidine | C15H17N5 267.3 | 4-phenyl-cyclo-hexanone | 1.55 | 268.49 |
| 24 | 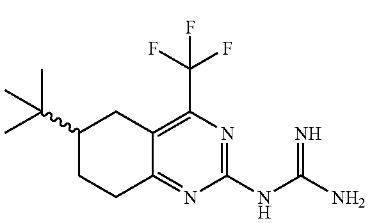 | N-(6-tert-butyl-4-trifluoromethyl-5,6,7,8-tetrahydro-quinazolin-2-yl)-guanidine | C14H20F3N5 315.3 | 4-tert-butyl-cyclo-hexanone | 1.75 | 316.4 |

TABLE 2-continued

Analytical data of the products of Examples 1-26

| Ex. | Structure | Name | Empirical formula Molecular weight | Starting product | $t_R$ [min] | MS data m/z $[M + H]^+$ |
|---|---|---|---|---|---|---|
| 25 | 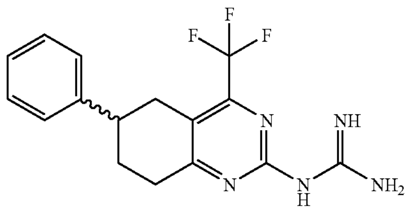 | N-(6-phenyl-4-trifluoromethyl-5,6,7,8-tetrahydro-quinazolin-2-yl)-guanidine | C16H16F3N5 335.3 | 4-phenyl-cyclo-hexanone | 1.68 | 336.35 |
| 26 | 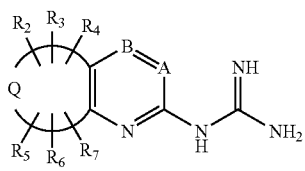 | N-(6-isopropyl-4-trifluoromethyl-5,6,7,8-etrahydro-quinazolin-2-yl)-guanidine | C13H18F3N5 301.3 | 4-isopropyl-cyclo-hexanone | 1.69 | 302.35 |

The invention claimed is:

1. A compound of formula (II)

in which

A represents N;

B represents a C atom substituted with $R_1$;

$R_1$ represents hydrogen or a lower alkyl, haloalkyl, alkylamino, cycloalkylamino, alkoxy, haloalkoxy or alkylthio group;

Q together with the pyrimidine ring forms a 6,7-dihydro-5H-cyclopentapyrimidine, 5,6,7,8-tetrahydro-quinazoline, 6,7,8,9-tetrahydro-5H-cycloheptapyrimidine or 5,6,7,8,9,10-hexahydrocyclooctapyrimidine skeleton;

$R_2$ means methyl, ethyl, n-propyl, isopropyl, n-butyl, isobutyl, tert.-butyl, 1,1-dimethylpropyl or phenyl;

$R_3$-$R_7$ mean hydrogen, alkyl, alkenyl, aryl, or cyanoalkyl;

or a pharmaceutically acceptable acid addition salt of such a compound.

2. A compound according to claim 1, in which $R_3$-$R_7$, if different from hydrogen, are each independently a lower alkyl;

or a pharmaceutically acceptable acid addition salt of such a compound.

3. A compound selected from the group consisting of:
N-(4-methyl-6-propyl-5,6,7,8-tetrahydro-quinazolin-2-yl)-guanidine;
N-(6-isopropyl-4-methyl-5,6,7,8-tetrahydro-quinazolin-2-yl)-guanidine;
N-(4,5-dimethyl-5,6,7,8-tetrahydro-quinazolin-2-yl)-guanidine; and
N-(6-tert-butyl-4-methyl-5,6,7,8-tetrahydro-quinazolin-2-yl)-guanidine;
or a pharmaceutically acceptable acid addition salt of such a compound.

4. A compound selected from the group consisting of:
N-(4-methyl-8-phenyl-5,6,7,8-tetrahydro-quinazolin-2-yl)-guanidine;
N-(4-methyl-6-phenyl-5,6,7,8-tetrahydro-quinazolin-2-yl)-guanidine;
N-[6-(1,1-dimethyl-propyl)-4-methyl-5,6,7,8-tetrahydro-quinazolin-2-yl]-guanidine;
N-(8-tert-butyl-4-methyl-5,6,7,8-tetrahydro-quinazolin-2-yl)-guanidine;
N-(4,6-dimethyl-5,6,7,8-tetrahydro-quinazolin-2-yl)-guanidine;
N-(4-methyl-6,7,8,9-tetrahydro-5H-cycloheptapyrimidin-2-yl)-guanidine;
N-(4-methyl-5,6,7,8,9,10-hexahydro-cyclooctapyrimidin-2-yl)-guanidine; and
N-(8-sec-butyl-4-methyl-5,6,7,8-tetrahydro-quinazolin-2-yl)-guanidine;
or a pharmaceutically acceptable acid addition salt of such a compound.

5. A compound selected from the group consisting of:
N-(4,8-dimethyl-5,6,7,8-tetrahydro-quinazolin-2-yl)-guanidine;
N-(8-allyl-4-methyl-5,6,7,8-tetrahydro-quinazolin-2-yl)-guanidine;
N-(6-isopropyl-5,6,7,8-tetrahydro-quinazolin-2-yl)-guanidine;
N-(6-tert-butyl-5,6,7,8-tetrahydro-quinazolin-2-yl)-guanidine;
N-(6-propyl-5,6,7,8-tetrahydro-quinazolin-2-yl)-guanidine;
N-(8-cyclohex-1-enyl-4-methyl-5,6,7,8-tetrahydro-quinazolin-2-yl)-guanidine; and
N-(6-tert-butyl-4-trifluoromethyl-5,6,7,8-tetrahydro-quinazolin-2-yl)-guanidine;
or a pharmaceutically acceptable acid addition salt of such a compound.

6. A compound selected from the group consisting of:
N-(6-phenyl-4-trifluoromethyl-5,6,7,8-tetrahydro-quinazolin-2-yl)-guanidine;
N-[8-(2-cyano-ethyl)-4-methyl-5,6,7,8-tetrahydro-quinazolin-2-yl]-guanidine; and
N-(6-isopropyl-4-trifluoromethyl-5,6,7,8-tetrahydro-quinazolin-2-yl)-guanidine;
or a pharmaceutically acceptable acid addition salt of such a compound.

7. A medicinal product comprising the compound according to any one of claims 1 or 3-6 and an inert carrier.

8. A compound according to claim 1, in which $R_1$ represents methyl, ethyl, trifluoromethyl, methylamino, ethylamino, isopropylamino, cyclopropylamino, methoxy, ethoxy, trifluoromethoxy, methylsulphanyl or ethylsulphanyl;
or a pharmaceutically acceptable acid addition salt of such a compound.

9. A compound according to claim 8, in which $R_1$ represents methyl or trifluoromethyl;
or a pharmaceutically acceptable acid addition salt of such a compound.

* * * * *